(12) United States Patent
Yazdandoost et al.

(10) Patent No.: US 9,824,254 B1
(45) Date of Patent: Nov. 21, 2017

(54) BIOMETRIC SENSING DEVICE WITH DISCRETE ULTRASONIC TRANSDUCERS

(71) Applicant: Apple Inc., Cupertino, CA (US)

(72) Inventors: Mohammad Yeke Yazdandoost, Waterloo (CA); Giovanni Gozzini, Cupertino, CA (US); Jean-Marie Bussat, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 149 days.

(21) Appl. No.: 14/590,821

(22) Filed: Jan. 6, 2015

Related U.S. Application Data

(60) Provisional application No. 62/057,802, filed on Sep. 30, 2014.

(51) Int. Cl.
| | |
|---|---|
| *G06K 9/00* | (2006.01) |
| *A61B 5/1172* | (2016.01) |
| *G06F 3/043* | (2006.01) |
| *G06F 3/041* | (2006.01) |

(52) U.S. Cl.
CPC .......... *G06K 9/0002* (2013.01); *A61B 5/1172* (2013.01); *G06F 3/0416* (2013.01); *G06F 3/0436* (2013.01); *G06K 9/00087* (2013.01)

(58) Field of Classification Search
None
See application file for complete search history.

(56) References Cited

U.S. PATENT DOCUMENTS

| | | | |
|---|---|---|---|
| 4,729,128 A | 3/1988 | Grimes | |
| 5,162,618 A | 11/1992 | Knowles | |
| 5,381,696 A | 1/1995 | Ichinose | |
| 5,515,298 A | 5/1996 | Bicz | |
| 5,589,636 A | 12/1996 | Bicz | |
| 5,719,950 A | 2/1998 | Osten | |
| 5,886,452 A | 3/1999 | Toda | |
| 6,091,406 A | 7/2000 | Kambara | |
| 6,159,149 A | 12/2000 | Erikson | |
| 6,164,135 A | 12/2000 | Bicz | |

(Continued)

FOREIGN PATENT DOCUMENTS

WO    WO 94/002911    2/1994

*Primary Examiner* — Amare Mengistu
*Assistant Examiner* — Sarvesh J Nadkarni
(74) *Attorney, Agent, or Firm* — Brownstein Hyatt Farber Schreck, LLP

(57) ABSTRACT

A biometric sensing system includes discrete ultrasonic transducers, a first electrode layer disposed over a first surface of the discrete ultrasonic transducers, and a second electrode layer disposed over a second surface of the discrete ultrasonic transducers. The first electrode layer may be a sheet of conductive material that is a common ground connection for the discrete ultrasonic transducers. Alternatively, the first electrode layer can be formed with discrete electrode elements, with a discrete electrode element disposed over the first surface of a discrete ultrasonic transducer. The second electrode layer may be formed with discrete electrode elements, with a discrete electrode element disposed over the second surface of one ultrasonic transducer. At least one integrated circuit can be attached and connected to one of the electrode layers. The integrated circuit includes drive circuits and sense circuits for the discrete ultrasonic transducers.

23 Claims, 6 Drawing Sheets

(56) References Cited

U.S. PATENT DOCUMENTS

| | | |
|---|---|---|
| 6,720,712 B2 | 4/2004 | Scott |
| 7,032,454 B2 | 4/2006 | Amano |
| 7,400,750 B2 | 7/2008 | Nam |
| 7,458,268 B2 | 12/2008 | Schneider et al. |
| 7,497,120 B2 | 3/2009 | Schneider et al. |
| 7,568,391 B2 | 8/2009 | Schneider et al. |
| 7,656,932 B2 | 2/2010 | Durand |
| 7,667,374 B2 | 2/2010 | Aono et al. |
| 7,734,435 B2 | 6/2010 | Thomas et al. |
| 7,739,912 B2 | 6/2010 | Schneider et al. |
| 7,770,456 B2 | 8/2010 | Stevenson et al. |
| 8,047,995 B2 | 11/2011 | Wakabayashi et al. |
| 8,054,203 B2 | 11/2011 | Breed et al. |
| 8,085,998 B2 | 12/2011 | Setlak et al. |
| 8,095,328 B2 | 1/2012 | Thomas et al. |
| 8,179,678 B2 | 5/2012 | Yamashita et al. |
| 8,201,739 B2 | 6/2012 | Schneider et al. |
| 8,335,356 B2 | 12/2012 | Schmitt |
| 8,345,508 B2 | 1/2013 | Wodnicki et al. |
| 8,508,103 B2 | 8/2013 | Schmitt et al. |
| 8,536,465 B2 | 9/2013 | Hagiwara et al. |
| 8,601,876 B2 | 12/2013 | Schneider et al. |
| 8,617,078 B2 | 12/2013 | Machida et al. |
| 8,666,126 B2 | 3/2014 | Lee et al. |
| 8,724,859 B2 | 5/2014 | Schneider et al. |
| 8,781,180 B2 | 7/2014 | Schneider et al. |
| 8,791,792 B2 | 7/2014 | Benkley, III |
| 8,982,089 B2 | 3/2015 | Lim |
| 9,044,171 B2 | 6/2015 | Venkatraman et al. |
| 9,100,034 B2 | 8/2015 | Oshima |
| 9,132,693 B2 | 9/2015 | Klootwijk et al. |
| 9,170,668 B2 | 10/2015 | Schneider et al. |
| 9,323,393 B2 | 4/2016 | Djordjev et al. |
| 9,465,972 B2 | 10/2016 | Chung et al. |
| 2003/0102777 A1 | 6/2003 | Kuniyasu et al. |
| 2003/0109993 A1 | 6/2003 | Peat et al. |
| 2004/0140735 A1 | 7/2004 | Scott et al. |
| 2004/0264746 A1 | 12/2004 | Polcha |
| 2005/0105784 A1* | 5/2005 | Nam ............... G06K 9/0002 382/124 |
| 2006/0196271 A1 | 9/2006 | Jancsik et al. |
| 2008/0142571 A1 | 6/2008 | Yokozuka et al. |
| 2008/0175450 A1 | 7/2008 | Scott |
| 2009/0167704 A1 | 7/2009 | Terlizzi et al. |
| 2010/0237992 A1* | 9/2010 | Liautaud ............ G06K 9/0002 340/5.83 |
| 2012/0092026 A1 | 4/2012 | Liautaud et al. |
| 2013/0015868 A1 | 1/2013 | Peng |
| 2014/0333328 A1* | 11/2014 | Nelson ............... G06F 3/044 324/663 |
| 2014/0352440 A1 | 12/2014 | Fennell et al. |
| 2014/0355381 A1 | 12/2014 | Lal et al. |
| 2014/0359757 A1 | 12/2014 | Sezan et al. |
| 2015/0053006 A1 | 2/2015 | DeCoux et al. |
| 2015/0185898 A1 | 7/2015 | Masson et al. |
| 2015/0189136 A1 | 7/2015 | Chung et al. |
| 2015/0192547 A1 | 7/2015 | Lee et al. |
| 2015/0358740 A1 | 12/2015 | Tsai et al. |
| 2016/0063300 A1 | 3/2016 | Du et al. |
| 2016/0117541 A1 | 4/2016 | Lu et al. |

* cited by examiner

BIOMETRIC SENSING DEVICE WITH DISCRETE ULTRASONIC TRANSDUCERS

CROSS-REFERENCE TO RELATED APPLICATIONS

This application claims the benefit under 35 U.S.C. §119(e) of U.S. Provisional Patent Application No. 62/057,802, filed Sep. 30, 2014, entitled "Biometric Sensing Device with Discrete Ultrasonic Transducers," the entirety of which is incorporated herein by reference.

TECHNICAL FIELD

The present invention relates to biometric sensing devices, and more particularly to a biometric sensing device that includes discrete ultrasonic transducers.

BACKGROUND

Many electronic devices, networks, and physical buildings include security features to prevent unauthorized access. For example, an electronic device can include a biometric sensing device, such as a fingerprint sensing device, that is used to verify a user's identity by determining whether captured biometric data matches known biometric data of an authorized user. The user is given access to the electronic device when the captured biometric data matches the known biometric data.

The performance of some biometric sensing devices may be adversely affected by conditions unrelated to the biometric sensing device itself. For example, a fingerprint sensing device can be sensitive to contaminants on a user's finger. Contaminants such as grease, lotion, dirt, sweat, and food particles on a finger can degrade a captured fingerprint image, which can prevent a fingerprint sensing device from matching the captured fingerprint image to a known fingerprint image. Alternatively, a finger contacting an input surface of the fingerprint sensing device with too much or too little pressure can reduce the quality of the captured fingerprint image and prevent the fingerprint sensing device from recognizing the user.

SUMMARY

Embodiments described herein provide an ultrasonic biometric sensing device. In one aspect, a biometric sensing system can include discrete ultrasonic transducers, a first electrode layer disposed over a first surface of the discrete ultrasonic transducers, and a second electrode layer disposed over a second surface of the discrete ultrasonic transducers. In one embodiment, the first and second electrode layers each include discrete electrode elements, where a discrete electrode element in the first electrode layer is disposed over the first surface of an ultrasonic transducer and a discrete electrode element in the second electrode layer is disposed over the second surface of the same ultrasonic transducer. A first integrated circuit is attached and electrically connected to the first electrode layer, and a second integrated circuit is attached and electrically connected to the second electrode layer. The first and second integrated circuits include drive circuits and sense circuits for the discrete ultrasonic transducers. The drive and sense circuits are operably connected to the discrete ultrasonic transducers through the discrete electrode elements in the first and/or second electrode layers.

In another aspect, a biometric sensing system can include discrete ultrasonic transducers, a first electrode layer disposed over a first surface of the discrete ultrasonic transducers, and a second electrode layer disposed over a second surface of the discrete ultrasonic transducers. The first electrode layer is a sheet of conductive material. The first electrode layer can act as a common ground or a common DC voltage connection for the discrete ultrasonic transducers. The second electrode layer includes discrete electrode elements, where a discrete electrode element is disposed over the first surface of an ultrasonic transducer. An integrated circuit is attached and electrically connected to the second electrode layer. The integrated circuit includes drive circuits and sense circuits for the discrete ultrasonic transducers. The drive and sense circuits are operably connected to the discrete ultrasonic transducers through the discrete electrode elements in the second electrode layer.

BRIEF DESCRIPTION OF THE DRAWINGS

Embodiments of the invention are better understood with reference to the following drawings. The elements of the drawings are not necessarily to scale relative to each other. Identical reference numerals have been used, where possible, to designate identical features that are common to the figures.

DETAILED DESCRIPTION

Figure 1:
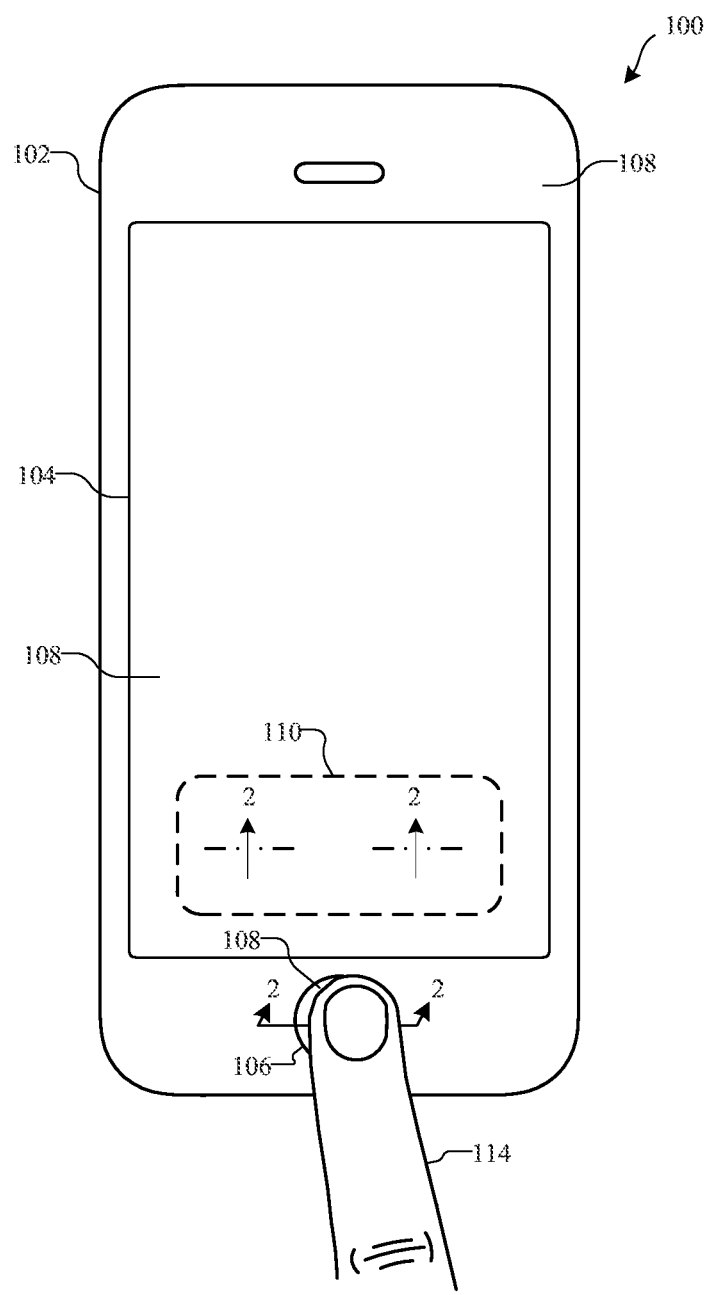
FIG. 1 is a plan view of an example device that is suitable to include an ultrasonic biometric sensing device.

Embodiments described herein provide a biometric sensing device that includes discrete ultrasonic transducers that are used to capture biometric data, such as a fingerprint. A first electrode layer is positioned over a first surface (e.g., top surface) of the discrete ultrasonic transducers. In one embodiment, the first electrode layer is formed with multiple discrete electrode elements, where a discrete electrode element is disposed over the first surface of one discrete ultrasonic transducer. A second electrode layer is disposed over a second surface (e.g., bottom surface) of the discrete ultrasonic transducers. The second electrode layer is formed with multiple discrete electrode elements, with a discrete electrode element disposed over the second surface of one discrete ultrasonic transducer. The discrete electrode elements in the first and second electrode layers are operably connected to drive circuits and sense circuits. The drive circuits are configured to generate drive signals that are applied to the ultrasonic transducers through the discrete electrode elements. The sense circuits are configured to sense signals generated by the discrete ultrasonic transducers in response to reflected sound waves. The drive and sense circuits can be included in a first integrated circuit that is attached and electrically connected to the first electrode layer, and in a second integrated circuit attached and electrically connected to the second electrode layer. In one non-limiting example, the first and second integrated circuits are application-specific integrated circuits (ASIC), but other types of integrated circuits can be used.

In another embodiment, the first electrode layer is formed with a sheet of conductive material that is disposed over the discrete electrode elements. The first electrode layer can act as a common ground connection, or as a common DC voltage connection, for the discrete ultrasonic transducers. The second electrode layer is disposed over a second surface (e.g., bottom surface) of the discrete ultrasonic transducers. The second electrode layer is formed with multiple discrete electrode elements, with a discrete electrode element disposed over the second surface of one discrete ultrasonic transducer. The discrete electrode elements are operably connected to drive circuits and sense circuits. The drive and sense circuits can be included in an integrated circuit that is attached and electrically connected to the second electrode layer.

When an image of a biometric subject (e.g., a finger) is to be captured, the drive circuits apply a drive signal to one or more discrete electrode elements. Based on the drive signal, the ultrasonic transducers operably connected to the one or more discrete electrode elements each generate a sound wave pulse. In one embodiment, the sound wave pulses collectively form a plane wave that propagates to the input surface of the ultrasonic biometric sensing device. A fraction of the sound waves reflect off the input surface, and the discrete ultrasonic transducers are used to detect the reflected sound waves. The reflected sound waves create dynamic pressure on the ultrasonic transducers, and the ultrasonic transducers produce an electrical signal that is proportional to the amount of pressure applied to the transducer. The signals obtained from the discrete ultrasonic transducers are used to construct the image of the biometric subject (e.g., a fingerprint image).

Referring now to FIG. 1, there is shown a plan view of an example device that is suitable to include an ultrasonic biometric sensing device. The electronic device 100 includes an enclosure 102, a display 104, and an input/output (I/O) device 106. The electronic device 100 can also include one or more internal components (not shown) typical of a computing or electronic device, such as, for example, one or more processors, memory components, network interfaces, and so on.

In the illustrated embodiment, the electronic device 100 is implemented as a smart telephone. Other embodiments, however, are not limited to this construction. Other types of computing or electronic devices can include an ultrasonic biometric sensing device, including, but not limited to, a netbook or laptop computer, a tablet computing device, a digital camera, a biometric sensing device used in conjunction with, for example, controlled access to a secured building or device, and a wearable electronic or communication device.

As shown in FIG. 1, the enclosure 102 can form an outer surface or partial outer surface and protective case for the internal components of the electronic device 100, and may at least partially surround the display 104. The enclosure 102 can be formed of one or more components operably connected together, such as a front piece and a back piece. Alternatively, the enclosure 102 can be formed of a single piece operably connected to the display 104.

The display 104 can be operably or communicatively connected to the electronic device 100. The display 104 can be implemented with any type of suitable display, such as a retina display, a color liquid crystal display (LCD), or an organic light-emitting display (OLED). The display 104 can provide a visual output for the electronic device 100 and/or function to receive user inputs to the electronic device. For example, the display 104 can be a multi-touch capacitive sensing touchscreen that can detect one or more user touch and/or force inputs.

The I/O device 106 can be implemented with any type of input or output device. By way of example only, the I/O device 106 can be a switch, a button, a capacitive sensor, or other input mechanism. The I/O device 106 allows a user to interact with the electronic device 100. For example, the I/O device 106 may be a button or switch to alter the volume, return to a home screen, and the like. The electronic device can include one or more input device and/or output devices, and each device can have a single I/O function or multiple I/O functions. Example I/O devices include a microphone, speakers, a touch sensor, network or communication ports, a display, and wireless communication devices.

A cover glass 108 can be disposed over some or all of an exterior top surface of the electronic device. In the illustrated embodiment, the cover glass 108 can be a flexible touchable surface that is made of any suitable transparent material, such as, for example, a glass, a plastic, or sapphire. In one embodiment, a cover glass 108 is positioned over the entire top surface of the electronic device (e.g., the enclosure 102, the display 104, and the I/O device 106). In the illustrated embodiment, a region of the cover glass can act as an input surface for the ultrasonic biometric sensing device. As one example, the region of the cover glass 108 over the I/O device 106 may be an input surface for the ultrasonic biometric sensing device. Additionally or alternatively, a region 110 of the cover glass 108 over the display 104 can be an input surface for the ultrasonic biometric sensing device.

The present invention is described herein in conjunction with an ultrasonic fingerprint sensing device, although other embodiments are not limited to a fingerprint sensing device. Images or data obtained from other biometric subjects may be captured in other embodiments.

An ultrasonic fingerprint sensing device can capture fingerprint images when one or more fingers, or a portion of a finger or fingers, is proximate to or touching an input surface of the ultrasonic fingerprint sensing device. For example, as shown in FIG. 1, an ultrasonic fingerprint sensing device may capture images when a finger 114 is near or in contact with the I/O device 106. In other embodiments, an ultrasonic fingerprint sensing device may capture fingerprint images when a finger is near or in contact with the region 110.

As used herein, the terms "image" and "fingerprint image" include an image, a composite image formed with multiple images, and other types of data that can be captured by an ultrasonic fingerprint sensing device. By way of example only, an ultrasonic fingerprint sensing device can produce a data structure that defines the features in a fingerprint. Additionally, the term "fingerprint image" is meant to encompass an image or other data relating to a fingerprint of some or all of one or more fingers, some or all of a palm, some or all of a hand, and various combinations thereof. The term "finger" is meant to encompass one or more fingers, thumbs, some or all of a palm, some or all of a hand, and various combinations thereof.

Figure 2A:
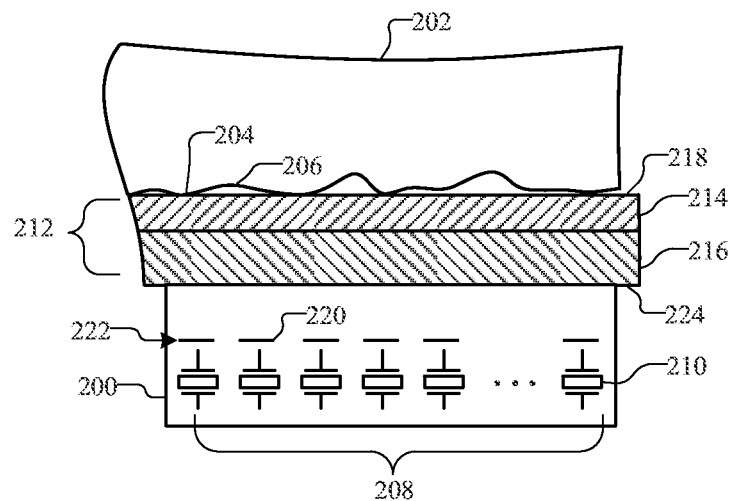
FIGS. 2A-2B are cross-sectional views of the electronic device 100 taken along line 2-2 in FIG. 1.
Figure 2B:
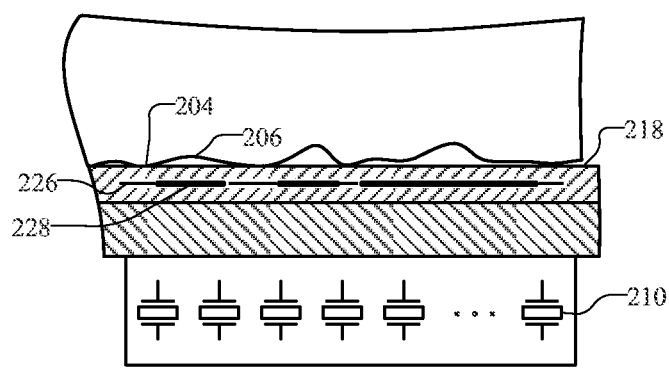

Operation of an ultrasonic fingerprint sensing system is now described. FIGS. 2A-2B are cross-sectional views of the electronic device 100 taken along line 2-2 in FIG. 1. The ultrasonic fingerprint sensing device 200 can capture a fingerprint image of at least a portion of a finger 202 by imaging the ridges 204 and valleys 206 that collectively form a fingerprint. The ultrasonic fingerprint sensing device 200 includes an array 208 of discrete ultrasonic transducers 210.

In the illustrated embodiment, multiple layers of material are disposed over the ultrasonic fingerprint sensing device 200. The multiple layers of material collectively form an upper element 212. As shown, the upper element 212 includes a top layer 214 and an intermediate layer 216. In other embodiments, the upper element can include one or more layers of material. The top layer 214 receives touch inputs from a user and has an exterior or top surface 218 that acts as an input surface for the ultrasonic fingerprint sensing device. In one embodiment, the discrete ultrasonic transducers 210 can be positioned transverse or substantially parallel to the input surface 218.

The upper element 212 can be a portion of a display (e.g., region 110 in FIG. 1), a portion of an input device (e.g., I/O device 106 in FIG. 1), or a portion of the enclosure of the electronic device. The upper element 212 can include active components (e.g., circuits, circuit traces, a display layer, and so on) or passive components (e.g., glass sheet, an adhesive layer, and so on) or a combination thereof.

For example, if the upper element 212 is included in region 110 in FIG. 1, the upper element 212 can include a cover glass (e.g., cover glass 108), a touch sensing device, a polarizing layer, a third conductive layer, a color filter layer, and a display layer such as an LCD or LED display layer. The touch sensing device may be constructed with a first conductive layer, an insulating layer, and a second conductive layer. As another example, if the upper element 212 is included in the I/O device 106 shown in FIG. 1, the upper element 212 may include a cover glass, an ink layer, an adhesive layer, and a flexible circuit that is operably connected to a switch.

When a fingerprint image is to be captured, drive circuits apply a drive pulse to the discrete electrode elements that are disposed over the discrete ultrasonic transducers (see e.g., discrete electrode element 410 in FIG. 4), which in turn causes the discrete ultrasonic transducers 212 to substantially simultaneously produce sound wave pulses 220 that collectively form a plane wave 222 that propagates through the upper element 212 from the bottom surface 224 towards the input surface 218. A fraction of the plane wave reflects at each material interface encountered by the plane wave. The plane wave confronts different types of interfaces at the input surface 218. One interface type exists between the top layer 214 and a ridge 204 of the finger 202. Another interface type exists between the top layer 214 and the air residing between the input surface 218 and a valley 206. Different fractions of the plane wave reflect from the different interface types. The fractions of the plane wave(s) that reflect at the two interface types is a function of the differences in acoustic impedance between the two elements at each interface type. The larger the change in acoustic impendence encountered by the plane wave, the larger the fraction of the plane wave reflected.

In other words, the interface at a ridge may reflect a first fraction of the sound waves, while the interface at a valley reflects a different second fraction of the sound waves. The acoustic impedance of skin is higher than the acoustic impedance of air, so the interface at a ridge generally reflects a smaller fraction of the sound waves than the interface at a valley. Since the properties of the reflected sound wave(s) exhibit the same characteristic pattern of the ridges and valleys in the finger, the measurements of the reflected sound waves can be used to construct a fingerprint image.

FIG. 2B depicts the plane wave reflecting off the input surface 218. Different regions of the plane wave (e.g., regions 226 and 228) are depicted with different line thicknesses to illustrate the different fractions of the plane wave reflecting off the different interface types. The fraction 226 of the plane wave reflecting from a location below a ridge 204 is less than the fraction 228 reflecting from a location below a valley 206.

The discrete ultrasonic transducers 210 can be used to detect the reflected sound waves after the discrete ultrasonic transducers emit the plane wave. As described earlier, the reflected sound waves create pressure on the ultrasonic transducers, and the ultrasonic transducers produce an electrical signal that is proportional to the amount of pressure applied to a respective transducer. Sense circuits (not shown) can read the signals from the discrete ultrasonic transducers 210 via the discrete electrode elements.

Although the plane wave has been described as being formed from a sound wave pulse that is generated by all of the ultrasonic transducers 210, those skilled in the art will recognize that a fingerprint image can be captured using only a portion or portions of the discrete ultrasonic transducers. The drive circuits can apply drive pulses to select discrete electrode elements. Similarly, the sense circuits can individually address and receive signals from select discrete electrode elements.

Figure 3:
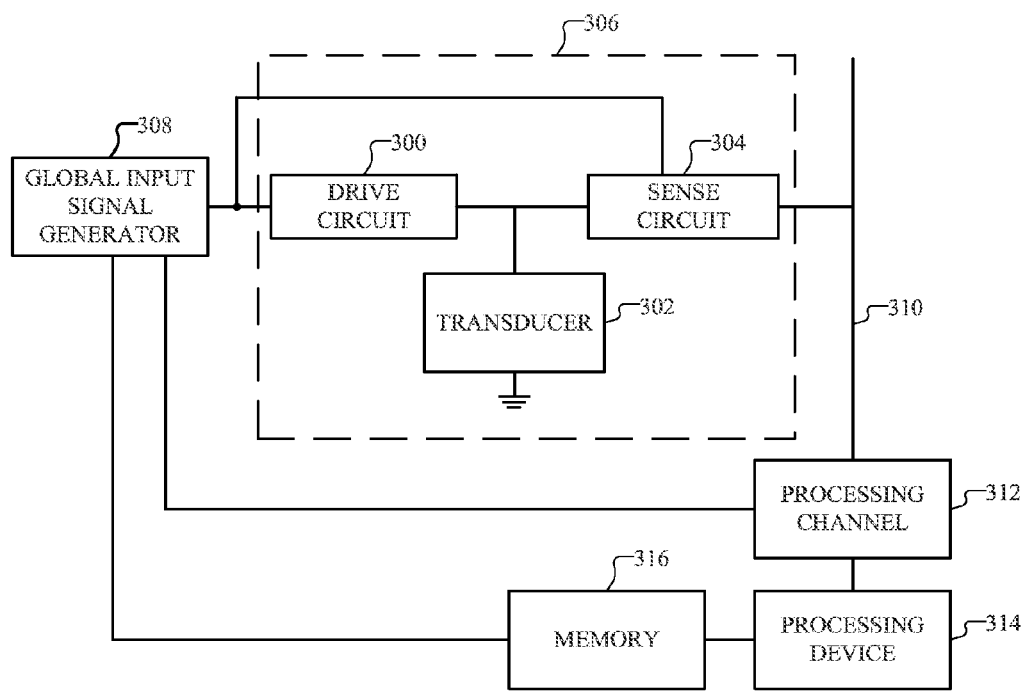
FIG. 3 is a block diagram of an ultrasonic fingerprint sensing system.

FIG. 3 is a block diagram of an ultrasonic fingerprint sensing system. A drive circuit 300 is operably connected to a discrete ultrasonic transducer 302. Similarly, a sense circuit 304 is operably connected to the discrete ultrasonic transducer 302. In some embodiments, the drive circuit 300, the discrete ultrasonic transducer 302, and the sense circuit 304 collective form a pixel or discrete ultrasonic sensor 306. Thus, a discrete ultrasonic sensor 306 has in-pixel circuitry to drive the discrete ultrasonic transducer and in-pixel circuitry to read the signal from the discrete ultrasonic transducer. Although FIG. 3 depicts only one discrete ultrasonic sensor 306, those skilled in the art will recognize that an ultrasonic fingerprint sensing system can include multiple discrete ultrasonic sensors.

A global input signal generator 308 may be operably connected to each drive circuit 300, to each sense circuit 304, and to a processing channel operably connected to the sense circuit 304. The global input signal generator 308 is configured to output control signals to control the timing and the function of the drive circuit 300, the sense circuit 304, and some or all of the circuits in the processing channel 312. In one embodiment, the global input signal generator 308 and the drive and sense circuits can be implemented in one integrated circuit. In another embodiment, the global input signal generator 308 and the sense circuits may be implemented in one integrated circuit and the drive circuits in another integrated circuit.

The sense circuit 304 is operably connected to a global output path 310 that operably connects to the processing channel 312. In one embodiment, the global output path 310 is operably connected to all of the sense circuits in a region (e.g., a column) of an array of discrete ultrasonic transducers. The processing channel receives and processes analog signals, digitizes the signals, and outputs the signals to a processing device 314. One example of a processing channel is described in conjunction with FIG. 10. In one embodiment, the processing channel and the sense circuits can be implemented in one integrated circuit. In another embodiment, the processing channel is implemented in one integrated circuit and the sense circuits in another integrated circuit.

The processing device 314 is configured to analyze the signals and construct a fingerprint image based on the signals received from the processing channel 312. The processing device 314 can be implemented as any electronic device capable of processing, receiving, or transmitting data or instructions. For example, the processing device can be a microprocessor, a central processing unit (CPU), an application-specific integrated circuit (ASIC), a digital signal processor (DSP), or combinations of multiple such devices. As described herein, the term "processing device" is meant to encompass a single processor or processing unit, multiple processors, multiple processing units, or other suitably configured computing element or elements.

A memory 316 may be operably connected to the global input signal generator 308 and/or the processing device 314. Timing signals and control data for the global input signal generator 308 may be stored in memory 316 and accessed by the global input signal generator 308. Additionally or alternatively, the signals received by the processing device 314 and/or the fingerprint image may be stored in memory 316. The memory 316 can be configured as any type of memory. By way of example only, memory 316 can be implemented as random access memory, read-only memory, Flash memory, removable memory, or other types of storage elements, in any combination.

Figure 4:
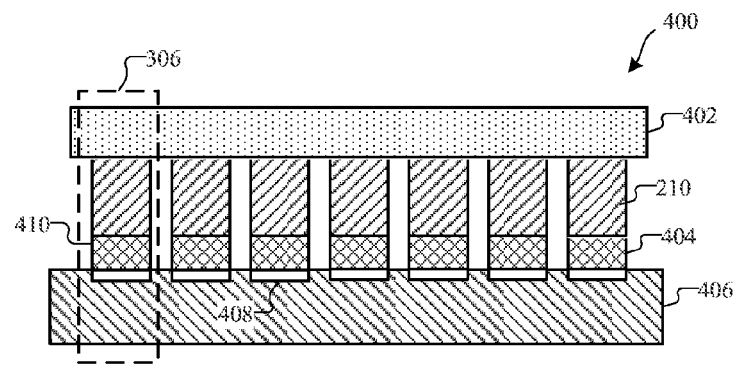
FIG. 4 is a cross-sectional view of one example of an ultrasonic fingerprint sensing device.

Referring now to FIG. 4, there is shown a cross-sectional view of one example of an ultrasonic fingerprint sensing device. The ultrasonic fingerprint sensing device 400 includes multiple discrete ultrasonic transducers 210. In one embodiment, the discrete ultrasonic transducers are made of a material having piezoelectric properties. One example material includes, but is not limited to, a lead zirconate titanate material. A different material having piezoelectric properties can be used in other embodiments.

A first electrode layer 402 is disposed over a first surface (e.g., a top surface) of the discrete ultrasonic transducers 210. The first electrode layer 402 is a common ground connection, or a common DC voltage connection, for the discrete ultrasonic transducers 210. The first electrode layer 402 can be made of any suitable conductive material. For example, the first electrode layer may be made of a metal including, for example, silver, copper, and gold. In other embodiments, the first electrode layer may be made of a non-metal conductive material, such as indium tin oxide (ITO).

A second electrode layer 404 is positioned over a second surface (e.g., bottom surface) of the discrete ultrasonic transducers 210. Like the first electrode layer 402, the second electrode layer 404 may be made of any suitable conductive material. For example, the second electrode layer can be made of a metal including, for example, silver, copper, and gold. In other embodiments, the second electrode layer may be made of a non-metal conductive material, such as indium tin oxide (ITO). The second electrode layer includes discrete electrode elements that are disposed between the second surface of the discrete ultrasonic transducers 210 and a substrate 406.

In the illustrated embodiment, the substrate 406 is positioned below the second electrode layer 404. In some embodiments, the substrate 406 can act as a support structure for the discrete ultrasonic transducers. In one embodiment, the substrate 406 may be configured as an integrated circuit that includes the drive circuits and the sense circuits for the ultrasonic fingerprint sensing device. Additionally, in some embodiments, the integrated circuit can include at least a portion of the processing channel that is operably connected to one or more sense circuits.

The integrated circuit 406 is attached and electrically connected to the second electrode layer 404. The second electrode layer 404 can electrically connect the ultrasonic transducers 210 to the integrated circuit through a conductive element (e.g., contact pads 408) disposed on the surface of the integrated circuit 406. Each contact pad can electrically connect to a drive circuit and to a sense circuit. In one non-limiting example, the integrated circuit is an application-specific integrated circuit (ASIC), but other types of integrated circuits can be used.

As shown in FIG. 4, a pixel or discrete ultrasonic sensor 306 is formed by the first electrode layer 402, a discrete electrode element 410 in the second electrode layer 404, the associated discrete ultrasonic transducer 210, and the drive circuit and the sense circuit in the integrated circuit 406 that are connected to the discrete electrode element 410. Thus, the ultrasonic fingerprint sensing device includes an array of discrete ultrasonic sensors 306.

Figure 5:
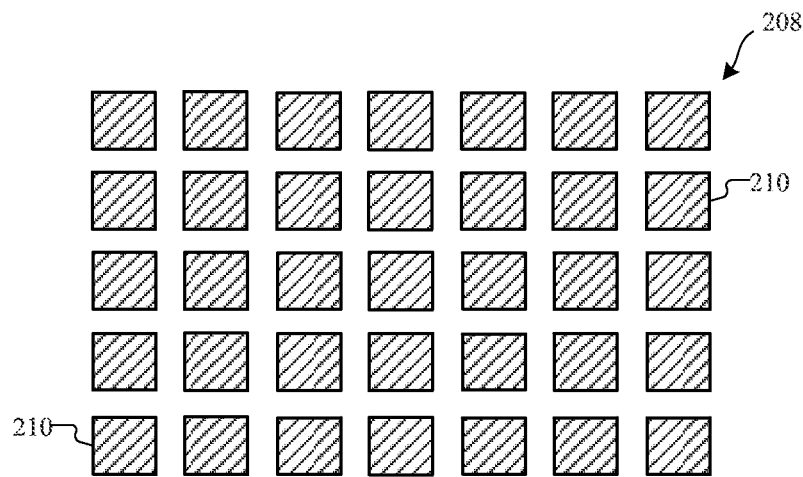
FIG. 5 is a plan view of the discrete ultrasonic transducers 210 shown in FIG. 4.

FIG. 5 is a plan view of the discrete ultrasonic transducers shown in FIG. 4. Each ultrasonic transducer 210 is separate and distinct from the other ultrasonic transducers 210. As shown in FIG. 5, the ultrasonic transducers can be arranged in rows and columns to form an array 208 of ultrasonic transducers. Although FIG. 5 depicts thirty-five discrete ultrasonic transducers, those skilled in the art will recognize that an ultrasonic fingerprint sensing device can include any number of discrete ultrasonic transducers. Additionally, a discrete ultrasonic transducer can have any suitable shape and dimensions. In other embodiments, the discrete ultrasonic transducers can be arranged in any suitable arrangement and/or orientation. As one example, the ultrasonic transducers may be arranged in two or more concentric circles around a central point or a central discrete ultrasonic transducer.

Figure 6:
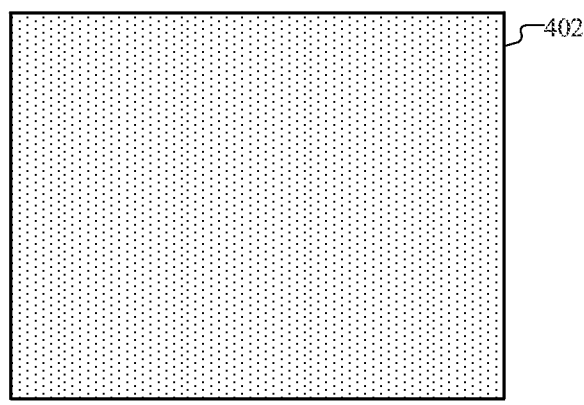
FIG. 6 is a plan view of one example of the first electrode layer 402 shown in FIG. 4.

Referring now to FIG. 6, there is shown a plan view of the first electrode layer 402 shown in FIG. 4. The first electrode layer 402 is formed with a sheet of conductive material. The sheet of conductive material is disposed over the discrete ultrasonic transducers. As described earlier, the first electrode layer 402 can be a common ground or common DC voltage connection for the discrete ultrasonic transducers 210.

Figure 7:
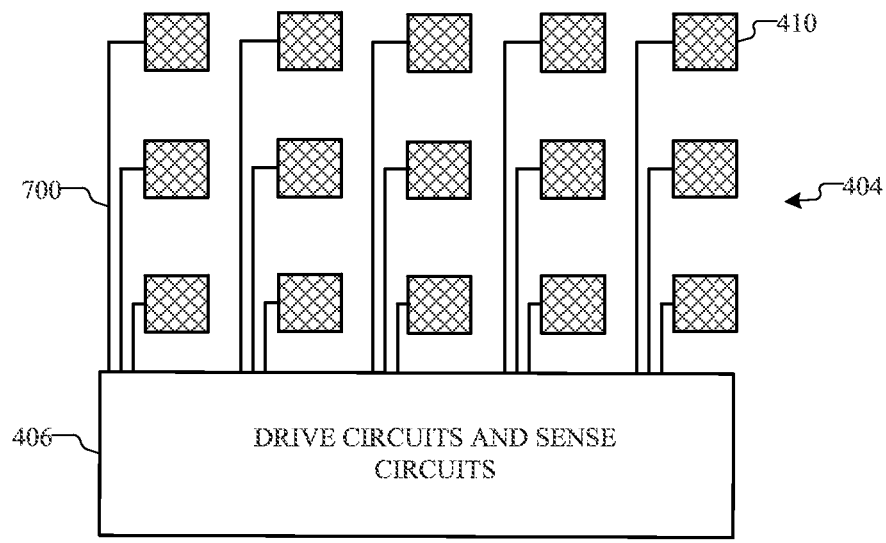
FIG. 7 is a plan view of the second electrode layer 404 shown in FIG. 4 operably connected to drive circuits and sense circuits.

FIG. 7 is a plan view of the second electrode layer 404 shown in FIG. 4 operably connected to drive circuits and sense circuits. The second electrode layer 404 is formed of discrete electrode elements 410. The integrated circuit 406 includes a drive circuit and a sense circuit (not shown) that are electrically connected to a discrete electrode element 410 by a conductive element 700. As described earlier, the drive circuits apply a drive signal to the discrete ultrasonic transducers 210 via respective discrete electrode elements 410, which in turn causes the discrete ultrasonic transducers to produce sound wave pulses. Fractions of the sound wave pulses reflect off the input surface of the ultrasonic fingerprint sensing device and are detected by respective discrete ultrasonic transducers. The sound wave pulses apply pressure to the discrete ultrasonic transducers. The piezoelectric material produces an electrical signal that is proportional to the amount of pressure on the piezoelectric material. The sense circuits read the electrical signals from the discrete ultrasonic transducers.

Figure 8:
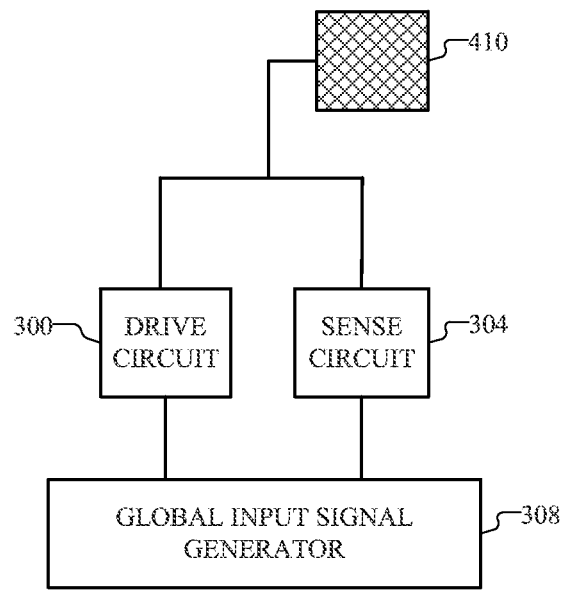
FIG. 8 is a block diagram of a discrete electrode element 410 operably connected to a drive circuit and a sense circuit.

Referring now to FIG. 8, there is shown a block diagram of a discrete electrode element 410 operably connected to a drive circuit and a sense circuit. The global input signal generator 308 outputs a first control signal that is received by the drive circuit 300. Based on the first control signal, the drive circuit 300 outputs a drive signal that is applied to the discrete electrode element 410. When the signal is to be read from the discrete ultrasonic transducer connected to the discrete electrode element 410, the global input signal generator 308 outputs a second control signal that is received by the sense circuit 304. Based on the second control signal, the sense circuit 304 reads the signal from the discrete ultrasonic transducer.

In some embodiments, the global input signal generator 308 can be a controller that controls the drive and sense operations (e.g., transmission of the first and second control signals) and controls the control signals for the processing channel 312. In other embodiments, a separate processing device (e.g., processing device 314) can control the operations of the global input signal generator 308. In other words, the global input signal generator or a separate processing device can control the two modes of the ultrasonic fingerprint sensing device. One mode is an integration mode, when the drive circuits apply drive signals to the discrete ultrasonic transducers and the discrete ultrasonic transducers responsively produce sound wave pulses that propagate to the input surface of the ultrasonic fingerprint sensing device. Another mode is an imaging mode, when the signals produced by the ultrasonic transducers in response to the reflected sound wave pulses are read from the discrete ultrasonic transducers and an image of the finger on the input surface is produced.

Figure 9:
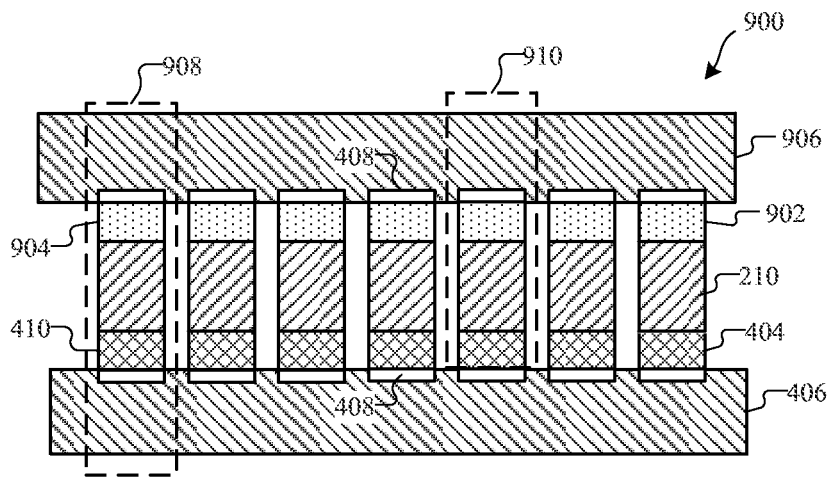
FIG. 9 is a cross-sectional view of another example of an ultrasonic fingerprint sensing device.

FIG. 9 is a cross-sectional view of another example of an ultrasonic fingerprint sensing device. The ultrasonic fingerprint sensing device 900 is similar to the embodiment shown in FIG. 4, except that the first electrode layer 902 is formed with discrete electrode elements 904 and a second integrated circuit 906 is attached and electrically connected to the first electrode layer 902. The discrete electrode elements 410 in FIG. 7 illustrate one example of the discrete electrode elements 904 in the first electrode layer 902.

The drive circuits and the sense circuits for the discrete ultrasonic transducers can be implemented in both the first and second integrated circuits 406, 906. In other words, the drive and sense circuits for some discrete ultrasonic transducers can be included in the first integrated circuit 406 while the drive and sense circuits for other discrete ultrasonic transducers can be implemented in the second integrated circuit 906. Alternatively, the drive circuits for the discrete ultrasonic transducers can be implemented in one integrated circuit (e.g., first integrated circuit) and the sense circuits for the discrete ultrasonic transducers may be implemented in the other integrated circuit (e.g., second integrated circuit).

The discrete ultrasonic transducers can be electrically connected to respective drive and sense circuits in the first and second integrated circuits through conductive elements (e.g., contact pads) 408. In embodiments where the drive and sense circuits for a discrete ultrasonic transducer 210 are implemented in a single integrated circuit, only a single conductive element 408 may be used for the discrete ultrasonic transducer.

When the drive and sense circuits for an ultrasonic transducer are included in both the first and second integrated circuits 906, 406, a pixel or discrete ultrasonic sensor 908 is formed by the discrete electrode element 904 in the first electrode layer 902, a discrete electrode element 410 in the second electrode layer 404, the discrete ultrasonic transducer 210 connected to the discrete electrode elements, and the drive and sense circuits in the first and second integrated circuits 406, 906. When the drive and sense circuits for an ultrasonic transducer are included in one integrated circuit (e.g., integrated circuit 906), a pixel or discrete ultrasonic sensor 910 is formed by the discrete electrode element 904 in the first electrode layer 902, a discrete electrode element 410 in the second electrode layer 404, the discrete ultrasonic transducer 210 connected to the discrete electrode elements, and the drive and sense circuits in the integrated circuit.

Figure 10:
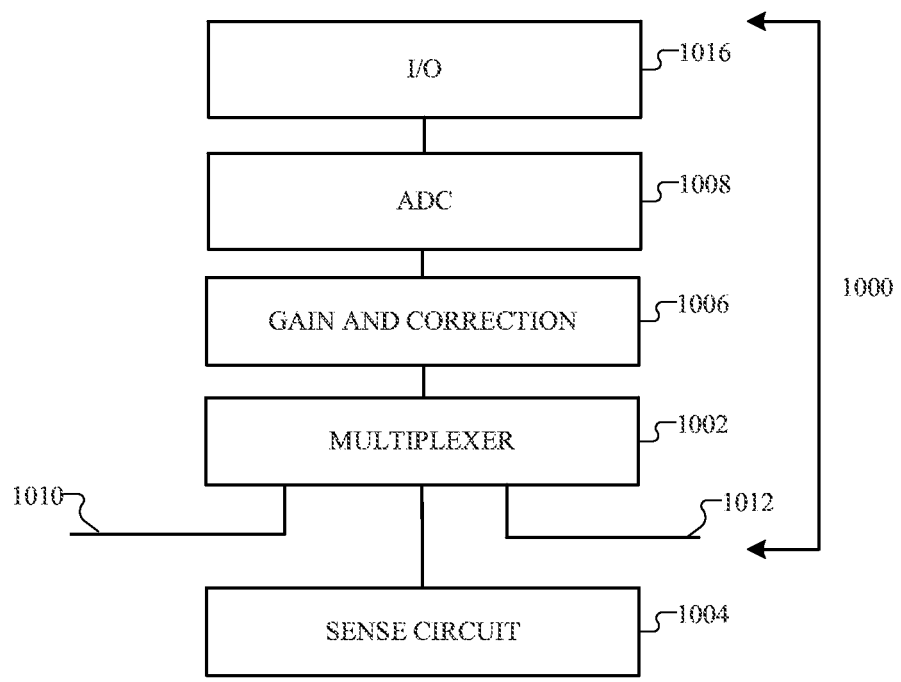
FIG. 10 is a block diagram of a sense circuit operably connected to an exemplar processing channel.

Referring now to FIG. 10, there is shown a block diagram of a sense circuit operably connected to an exemplar processing channel. The illustrated processing channel 1000 receives and processes analog signals, digitizes the signals, and outputs the signals to the processing device (not shown). The processing channel 1000 can include a multiplexer(s) 1002 operably connected to the outputs of the sense circuits 1004, gain and correction circuitry 1006 operably connected to the outputs of the multiplexer(s) 1002, and analog-to-digital converter(s) (ADCs) 1008 operably connected to the outputs of the gain and correction circuitry 1006. In some embodiments, the gain and correction circuitry is implemented as gain circuitry only. Example gain circuitry includes, but is not limited to, amplifiers. In some embodiments, the gain and correction circuitry may be implemented in a pixel or discrete ultrasonic sensor.

In some embodiments, the number of columns in the array of discrete ultrasonic transducers can be greater than the number of analog channels in the processing channel. In such embodiments, a multiplexer is coupled to the input of a gain and correction circuit and configured to multiplex multiple analog signals on signal lines 1010, 1012 from associated sense circuits to a particular ADC.

The ADCs convert the analog signals to digital signals. The outputs of the ADCs 1008 are operably connected to input/output (I/O) circuitry 1016. Low voltage differential signaling is one example of I/O circuitry. In some embodiments, data formatter circuitry (not shown) may be operably connected between the ADCs 1008 and the I/O circuitry 1016.

In some embodiments, the processing channel, or a portion of the processing channel, may be included in at least one of the integrated circuits (e.g., 406, 906 in FIG. 9).

Embodiments can employ any suitable circuit design for the drive circuit and the sense circuit. Thus, any suitable circuit topology may be included in a pixel or discrete ultrasonic sensor. For example, in one embodiment, a readout architecture can use a passive pixel architecture. Alternatively, other embodiments can employ an active pixel architecture for the readout architecture. Additionally, in some embodiments one or more circuits in the drive circuit and/or sense circuit may be shared by two or more pixels or discrete ultrasonic sensors. When one or more circuits are shared by two or more pixels, the patterning of the first electrode layer and/or the second electrode layer may be different to support the shared architecture.

Various embodiments have been described in detail with particular reference to certain features thereof, but it will be understood that variations and modifications can be effected within the spirit and scope of the disclosure. Even though specific embodiments have been described herein, it should be noted that the application is not limited to these embodiments. In particular, any features described with respect to one embodiment may also be used in other embodiments, where compatible. Likewise, the features of the different embodiments may be exchanged, where compatible.

We claim:

1. A biometric sensing system, comprising:
   a first discrete ultrasonic transducer;
   a second discrete ultrasonic transducer;
   a first electrode layer comprising a sheet of conductive material disposed over a first surface of the first and the second discrete ultrasonic transducers;
   a second electrode layer comprising a first discrete electrode element disposed over a second surface of the first discrete ultrasonic transducer and a second discrete electrode element disposed over the second surface of the second discrete ultrasonic transducer; and
   an integrated circuit attached and electrically connected to the second electrode layer, the integrated circuit comprising:
      a first drive circuit operably connected to the first discrete ultrasonic transducer through the first discrete electrode element in the second electrode layer;
      a first sense circuit operably connected to the first discrete ultrasonic transducer through the first discrete electrode element in the second electrode layer;
      a second drive circuit operably connected to the second discrete ultrasonic transducer through the second discrete electrode element in the second electrode layer; and
      a second sense circuit operably connected to the second discrete ultrasonic transducer through the second discrete electrode element in the second electrode layer.

2. The biometric sensing system as in claim 1, wherein the first electrode layer comprises a common ground or a common DC voltage connection for the discrete ultrasonic transducers.

3. The biometric sensing device as in claim 1, wherein the integrated circuit further includes a processing channel operably connected to the first and the second sense circuits.

4. The biometric sensing system as in claim 1, wherein the biometric sensing device comprises a fingerprint sensing device.

5. A biometric sensing system, comprising:
   a first discrete ultrasonic transducer;
   a second discrete ultrasonic transducer;
   a first electrode layer disposed over a first surface of the first and the second discrete ultrasonic transducers, the first electrode layer comprising a first discrete electrode element disposed over the first surface of the first ultrasonic transducer and a second discrete electrode element disposed over the first surface of the second ultrasonic transducer;
   a second electrode layer disposed over a second surface of the first and the second discrete ultrasonic transducers, the second electrode layer comprising third discrete electrode element disposed over the second surface of the first ultrasonic transducer and a fourth discrete electrode element disposed over the first surface of the second ultrasonic transducer;
   a first integrated circuit attached and electrically connected to the first electrode layer; and
   a second integrated circuit attached and electrically connected to the second electrode layer, wherein the first and second integrated circuits include:
      a first drive circuit and a first sense circuit that are operably connected to the first discrete ultrasonic transducer through the first and second sets of discrete electrode elements; and
      a second drive circuit and a second sense circuit that are operably connected to the second discrete ultrasonic transducer through the first and second sets of discrete electrode elements.

6. The biometric sensing device as in claim 5, wherein at least one of the first and second integrated circuits further includes a processing channel operably connected to one or more sense circuits.

7. The biometric sensing system as in claim 5, wherein the biometric sensing device comprises a fingerprint sensing device.

8. An electronic device, comprising:
   a biometric sensing device comprising:
      an array of discrete ultrasonic transducers;
      a first electrode layer comprising a sheet of conductive material disposed over a first surface of the array of discrete ultrasonic transducers;
      a second electrode layer comprising a first discrete electrode element disposed over a second surface of one of the array of ultrasonic transducers and a second discrete electrode element disposed over the second surface of another of the array of ultrasonic transducers; and
      an integrated circuit attached and electrically connected to the second electrode layer, wherein the integrated circuit includes drive circuits and sense circuits that are operably connected to the array of discrete ultrasonic transducers, with one of the drive circuits and one of the sense circuits coupled to one of the ultrasonic transducers through one of the discrete electrode elements in the second electrode layer; and
   an upper element that includes at least one layer of material disposed over the ultrasonic biometric sensing device, wherein an exterior surface of the upper element is an input surface for the biometric sensing device.

9. The electronic device as in claim 8, wherein the discrete ultrasonic transducers are positioned transverse to the input surface.

10. The electronic device as in claim 8, further comprising a processing channel operably connected to one or more sense circuits.

11. The electronic device as in claim 10, further comprising a processing device operably connected to the processing channel.

12. The electronic device as in claim 8, wherein the electronic device comprises a smart telephone.

13. The electronic device as in claim 8, wherein the biometric sensing device is disposed below an input/output device in the electronic device.

14. The electronic device as in claim 13, wherein the input/output device comprises a button.

15. The electronic device as in claim 8, wherein the biometric sensing device is disposed below a display in the electronic device.

16. An electronic device, comprising:
   a biometric sensing device comprising:
      discrete ultrasonic transducers;
      a first electrode layer disposed over a first surface of the discrete ultrasonic transducers, the first electrode layer comprising comprises a first set of discrete electrode elements with one discrete electrode element disposed over the first surface of an ultrasonic transducer;
      a second electrode layer disposed over a second surface of the discrete ultrasonic transducers, the second electrode layer comprising a second set of discrete electrode elements with one discrete electrode element disposed over the second surface of an ultrasonic transducer;

a first integrated circuit attached and electrically connected to the first electrode layer; and a second integrated circuit attached and electrically connected to the second electrode layer, wherein the first and second integrated circuits comprise a set of drive circuits and a set of sense circuits, each drive circuit and sense circuit operably connected to a distinct discrete ultrasonic transducer through the first and second sets of discrete electrode elements; and an upper element that includes at least one layer of material disposed over the ultrasonic biometric sensing device, wherein an exterior surface of the upper element is an input surface for the biometric sensing device.

17. The electronic device as in claim 16, wherein the discrete ultrasonic transducers are positioned transverse to the input surface.

18. The electronic device as in claim 16, further comprising a processing channel operably connected to one or more sense circuits.

19. The electronic device as in claim 18, further comprising a processing device operably connected to the processing channel.

20. The electronic device as in claim 16, wherein the electronic device comprises a smart telephone.

21. The electronic device as in claim 16, wherein the biometric sensing device is disposed below an input/output device in the electronic device.

22. The electronic device as in claim 21, wherein the input/output device comprises a button.

23. The electronic device as in claim 16, wherein the biometric sensing device is disposed below a display in the electronic device.

* * * * *